(12) United States Patent
Myeong et al.

(10) Patent No.: US 11,040,016 B2
(45) Date of Patent: Jun. 22, 2021

(54) COMPOSITION FOR ALLEVIATING, PREVENTING OR TREATING FEMALE MENOPAUSAL SYMPTOMS, CONTAINING, AS ACTIVE INGREDIENT, PINITOL, D-CHIRO-INOSITOL OR ANALOG COMPOUNDS THEREOF

(71) Applicant: DY NATURAL CO., LTD, Daejeon (KR)

(72) Inventors: Hyeon Koon Myeong, Daejeon (KR); Kwang Kyu Kim, Daejeon (KR)

(73) Assignee: DY NATURAL CO., LTD, Daejeon (KR)

( * ) Notice: Subject to any disclaimer, the term of this patent is extended or adjusted under 35 U.S.C. 154(b) by 0 days.

(21) Appl. No.: 16/339,786

(22) PCT Filed: Oct. 6, 2016

(86) PCT No.: PCT/KR2016/011203
§ 371 (c)(1),
(2) Date: Apr. 5, 2019

(87) PCT Pub. No.: WO2018/066730
PCT Pub. Date: Apr. 12, 2018

(65) Prior Publication Data
US 2020/0038339 A1 Feb. 6, 2020

(51) Int. Cl.
*A61K 31/047* (2006.01)
*A61P 5/30* (2006.01)

(52) U.S. Cl.
CPC .............. *A61K 31/047* (2013.01); *A61P 5/30* (2018.01)

(58) Field of Classification Search
CPC ..... A61K 31/047; A61K 31/075; A23L 33/10; A61P 15/12; A61P 5/30
See application file for complete search history.

(56) References Cited

U.S. PATENT DOCUMENTS

| | | | | |
|---|---|---|---|---|
| 4,924,023 A * | 5/1990 | Hobbs | ...................... | C07F 9/117 558/155 |
| 4,937,390 A * | 6/1990 | Faug | ........................ | C07C 35/48 239/70 |
| 5,124,360 A | 6/1992 | Larner et al. | | |
| 5,550,166 A * | 8/1996 | Ostlund | .................... | A61P 3/06 514/715 |
| 5,827,896 A | 10/1998 | Ostlund et al. | | |
| 8,273,718 B2 * | 9/2012 | Rho | ........................ | A61P 37/00 514/23 |
| 9,725,739 B2 * | 8/2017 | Myeong | .................... | C12P 7/18 |
| 2014/0010870 A1 * | 1/2014 | Unfer | ....................... | A61P 15/08 424/455 |

FOREIGN PATENT DOCUMENTS

| | | | |
|---|---|---|---|
| EP | 2502622 A1 | 9/2012 | |
| EP | 3375439 A1 | 9/2018 | |
| JP | 2008-536851 A | 9/2008 | |
| JP | 2010-538057 A | 12/2010 | |
| KR | 10-0844363 B1 | 7/2008 | |
| KR | 10-1225566 B1 | 1/2013 | |
| KR | 10-1671502 B1 | 11/2016 | |
| WO | WO-96/29063 A2 | 9/1996 | |
| WO | WO-2008142701 A1 * | 11/2008 | ........... A23C 20/005 |
| WO | WO-2009-031819 A2 | 3/2009 | |

OTHER PUBLICATIONS

D'Anna et al., "Effects of a New Flavonoid and Myo-Inositol Supplement on Some Biomarkers of Cardiovascular Risk in Postmenopausal Women: A Randomized Trial", 2014,International Journal of Endocrinology, vol. 2014, Article ID 653561, pp. 1-7. [doi.org/10.1155/2014/653561] (Year: 2014).*

F. Parazzini, "Resveratrol, inositol, vitamin D and K in the prevention of cardiovascular and osteoporotic risk: a novel approach in peri- and postmenopause", 2014, Minerva Ginecol., 66(5), pp. 513-518. (Year: 2014).*

Gullo et al., "Myo-inositol: from induction of ovulation to menopausal disorder management", 2015, Minerva Ginecol., 67(5), pp. 485-486. (Year: 2015).*

Thomas et al., "The "Other" Inositols and Their Phosphates: Synthesis, Biology, and Medicine (with Recent Advances in myo-Inositol Chemistry)", 2016 (Published online: Dec. 22, 2015), Angew. Chem. Int. Ed., 55(5), pp. 1614-1650. (Year: 2016).*

Extended European Search Report dated Sep. 12, 2019, issued in European Patent Application No. 16918351.4.

Carlomagno Gianfranco et al, "Myo-inositol in the treatment of premenstrual dysphoric disorder", Human Psychopharmacology, 2011, pp. 526-530.

John E. Nestler et al, "Ovulatory and Metabolic Effects of D-Chiro-Inositol in the Polycystic Ovary Syndrome", The New England Journal of Medicine, 1999, pp. 1314-1320.

M. Nordio et al, "The Combined therapy with myo-inositol and D-Chiro-inositol reduces the risk of metabolic disease in PCOS overweight patients compared to myo-inositol supplementation alone", European Review for Medical and Pharmacological Sciences, 2012, pp. 575-581.

(Continued)

*Primary Examiner* — My-Chau T. Tran
(74) *Attorney, Agent, or Firm* — Harness, Dickey & Pierce, P.L.C.

(57) ABSTRACT

The present invention relates to a use of D-chiro-inositol, pinitol, or analog compounds thereof for preventing or treating female menopausal symptoms. The active ingredient compound of the present invention has an effect of increasing the activity of female hormones by increasing the blood concentration of 17β-estradiol and lowering the blood concentration of sex hormone-binding globulin. Therefore, the active ingredient compound of the present invention can be developed as a drug or a nutraceutical for preventing, alleviating or treating female menopausal symptoms. The active ingredient of the present invention is derived from a natural product, and thus, unlike an agonist of female sex hormones or chemically synthesized sex hormones, has very few side effects when applied to the human body.

3 Claims, 10 Drawing Sheets

(56) References Cited

OTHER PUBLICATIONS

Thamaraiselvan Rengarajan et al, "D-Pinitol Promotes Apoptosis in MCF-7 Cells via Induction of p53 and Bax and Inhibition of Bcl-2 and NF-?B", Asian Pacific Journal of Cancer Prevention, 2014, pp. 1757-1762.
David C. Baker et al, "Synthesis and Evaluation of a Series of 2'-O-Acyl Derivatives of 9-?-D-Arabinofuranosyladenine as Antiherpes Agents", J. Med. Chem, 1984, pp. 270-274.
International Search Report from corresponding PCT Application No. PCT/KR2016/011203, dated Jun. 30, 2017.
Notice of Reasons for Refusal of JP Patent Application No. 2019-518411 dated Jun. 9, 2020.
Kamara, B. I., et al.; Phenolic Metabolites from Honeybush Tea (*Cyclopia subternata*), Journal of Agricultural and Food Chemistry, 2004, 52, 17, pp. 5391-5395.
Ferrari, F., et al.; "Diabetes, Fetal Programming and Metabolism"., American Journal of Obstetrics and Gynecology, 2016, 214, 1, pp. S49-S50.
Heimark, D., et al.; "Decreased myo-inositol to chiro-inositol (M/C) ratios and increased M/C epimerase activity in PCOS theca cells demonstrate increased insulin sensitivity compared to controls", Endocrine Journal 2014, 61 (2), 111-117.

\* cited by examiner

COMPOSITION FOR ALLEVIATING, PREVENTING OR TREATING FEMALE MENOPAUSAL SYMPTOMS, CONTAINING, AS ACTIVE INGREDIENT, PINITOL, D-CHIRO-INOSITOL OR ANALOG COMPOUNDS THEREOF

CROSS-REFERENCE TO RELATED APPLICATION

This application is a national phase application of PCT Application No. PCT/KR2016/011203, filed on 6 Oct. 2016. The entire disclosure of the application identified in this paragraph is incorporated herein by reference.

FIELD

The present invention relates to a composition containing pinitol or a pinitol-like compound or D-chiro-inositol or a D-chiro-inositol-like compound as an active ingredient for alleviation, prevention, or treatment of female menopause symptoms.

BACKGROUND

Menopause, sometimes called climacterium, refers to the time when woman's menstrual periods stop permanently. When women's ovarian functions deteriorate due to aging, ovulation and female hormone production are no longer attained, thus resulting in menopause. During menopause, the production of female hormones, such as estrogen and progesterone, is gradually reduced. Menopause usually appears between the ages of 45-55, and some women become menopausal early due to surgery or premature ovarian failure. One of the most common symptoms of menopause is irregular menstruation. Approximately 50% of menopausal women in Korea are known to undergo acute female hormone deficiency symptoms (e.g., hot flushes, sweating, etc.). Approximately 20% of menopausal women undergo more severe menopausal symptoms, and therefore suffer from, for example, hot flushes, fatigue, anxiety, depression, memory impairment, and sleep disorder. One of the methods used to prevent or treat these menopausal symptoms is hormone therapy. Hormone therapy employs estrogen therapy alone or combination therapy of estrogen and progestin. Hormone therapy is one of the therapies that are proven to most effectively reduce menopausal symptoms, but it is known that hormone therapy is highly likely to cause thrombosis, heart attack, stroke, breast cancer, and gallstone disease in some women.

Pinitol has a similar chemical structure and biochemical actions to inositol, and is a compound isolated from *Bougainvillea spectabilis*, sugar pine (*Pinus lambertiana*), and the like. D-chiro-inositol (DCI) is a compound that belongs to the inositol family. It is known that pinitol is converted into D-chiro-inositol in vivo. Various prior art documents disclose that pinitol, D-chiro-inositol, and derivatives thereof have a variety of biological activities, such as anti-diabetic, anti-inflammatory, and anti-cancer effects (WO 96/29063, U.S. Pat. Nos. 5,827,896, and 5,124,360).

The patent documents and references mentioned herein are incorporated by reference to the same extent as if each reference is individually and clearly specified by reference.

SUMMARY

Technical Problem

The present inventors researched and endeavored to find an active substance capable of alleviating female menopause symptoms. As a result, the present inventors verified that pinitol and D-chiro-inositol can be developed as a drug or functional food capable of preventing, alleviating, or treating female menopause symptoms by increasing the female hormone levels in the blood and decreasing the sex-hormone binding globulin (SHBG) level in the blood, and thus the present inventors completed the present invention.

Therefore, an aspect of the present invention is to provide a pharmaceutical composition containing pinitol or a pinitol-like compound or D-chiro-inositol or a D-chiro-inositol-like compound as an active ingredient for prevention or treatment of female menopause symptoms.

Another aspect of the present invention is to provide a food composition containing pinitol or a pinitol-like compound or D-chiro-inositol or a D-chiro-inositol-like compound as an active ingredient for prevention or alleviation of female menopause symptoms.

Still another aspect of the present invention is to provide a method for prevention or treatment of female menopause symptoms, the method including administering a composition to a subject in need thereof, the composition containing pinitol or a pinitol-like compound or D-chiro-inositol or a D-chiro-inositol-like compound as an active ingredient.

Other purposes and technical features of the present invention will be more specifically presented by the detailed description, claims, and drawings below.

Technical Solution

In accordance with an aspect of the present invention, there is provided a pharmaceutical composition containing pinitol or a pinitol-like compound or D-chiro-inositol or a D-chiro-inositol-like compound as an active ingredient for prevention, or treatment of female menopause symptoms.

In the present invention, "pinitol", which is the active ingredient of the composition, is represented by chemical formula 1 below.

[Chemical formula 1]

As used herein, the term "pinitol-like compound" refers to a collective term of compounds that share common functional and structural features with pinitol and thus retain the physiological activities of the present invention, equivalent to that of "pinitol" after direct or in vivo metabolic processes.

In the present invention, the "pinitol-like compound" includes suitable "derivatives" or "metabolites" of pinitol, "pinitol-containing compounds", or "pro-drugs of pinitol".

In the present invention, the suitable "derivatives" or "metabolites" of pinitol include, but are not limited to, pinitol glycosides, pinitol phospholipids, esterified pinitol, lipid-bound pinitol, pinitol phosphates, pinitol phytates, or mixtures thereof.

In the present invention, the "pinitol-containing compounds" mean compounds containing a pinitol moiety as one moiety of a larger structure. The "pinitol-containing compounds" include, but are not limited to, polysaccharides containing pinitol and one or more additional sugars or sugar derivatives, or complexes or chelate compounds of pinitol and one or more metal ions.

In the present invention, the "pro-drugs of pinitol" means compounds, as derivatives of pinitol, which are converted genuine pinitol in vivo by an enzymatic or chemical process and exhibit more improved delivery characteristics and/or therapeutic efficacy. Methods for manufacturing pro-drugs of sugars, for example, pro-drugs of sugars in the form of a methylated or acetylated hydroxyl group, and methods for administering the pro-drugs of sugars are well known in the art (Baker et al., J. Med. Chem., 27:270-274, 1984).

The pinitol and pinitol-like compound can be obtained through extraction and purification from a number of plants, such as pine needles, chick peas, *bougainvillea* leaves, alfalfa, carob, buckwheat, and *Cucurbita ficifolia*, or through other synthesis processes.

In the present invention, "D-chiro-inositol", which is the active ingredient of the composition, is represented by chemical formula 2 below.

[Chemical formula 2]

As used herein, the term "D-chiro-inositol-like compound" refers to a collective term of compounds that share common functional and structural features with "D-chiro-inositol" and thus retains the physiological activities of the present invention, equivalent to that of "D-chiro-inositol" after direct or in vivo metabolic processes.

The "D-chiro-inositol-like compound" includes "suitable derivatives or metabolites of D-chiro-inositol", "D-chiro-inositol-containing compounds", or "pro-drugs of D-chiro-inositol".

The "suitable derivatives or metabolites of D-chiro-inositol" can include, but are not limited to, D-chiro-inositol phosphates, D-chiro-inositol esters, D-chiro-inositol acetates, D-chiro-inositol ether, D-chiro-inositol lower alkyl ethers, D-chiro-inositol acetals, or D-chiro-inositol ketals.

The "D-chiro-inositol-containing compounds" mean compounds containing a D-chiro-inositol moiety as one moiety of a larger structure.

The "D-chiro-inositol-containing compounds" may be, but are not limited to, polysaccharides containing D-chiro-inositol and one or more additional sugars or sugar derivatives, D-chiro-inositol-phospholipids, or complexes or chelate compounds of D-chiro-inositol with one or more metal ions.

The "pro-drugs of D-chiro-inositol" mean compounds, as derivatives of D-chiro-inositol, which are converted genuine D-chiro-inositol in vivo by an enzymatic or chemical process and exhibit more improved delivery characteristics and/or therapeutic efficacy. Methods for manufacturing pro-drugs of sugars, for example, pro-drugs of sugars in the form of a methylated or acetylated hydroxyl group, and methods for administering the pro-drugs of sugars are well known in the art (Baker et al., J. Med. Chem., 27:270-274, 1984).

The D-chiro-inositol or D-chiro-inositol-like compound can be obtained through extraction and purification from natural plants, such as pine needles, chick peas, *bougainvillea* leaves, alfalfa, carob, buckwheat, and *Cucurbita ficifolia*, by performing an epimerase treatment on myo-inositol, or through chemical synthesis.

The pinitol or D-chiro-inositol of the present invention increases the production and activity of estradiol, a female sex hormone. Therefore, the pinitol or D-chiro-inositol can be used for treatment, prevention, or alleviation of female menopause symptoms.

In the present invention, the term "female menopause symptoms" refers to symptoms occurring during menopause, during which production and activities of female hormones are reduced by gradual loss of ovarian functions in women. An example of the female hormones, of which activities and production are reduced during the menopause, may be estrogens. The estrogen is a collective term of estrone, estradiol, and estriol hormones, and out of these, estradiol is the most potent female hormone.

In the present invention, the female menopause symptoms include, specifically, hot flushes, night sweating, irregular menstrual cycles, reduction of sexual desire, vaginal dryness, fatigue, hair loss, sleeping disorder, concentration disorder, memory loss, dizziness, weight gain, urinary incontinence, abdominal bloating, allergies, brittle nails, change in body odor, irregular heartbeat, depression, anxiety, nervousness, or panic disorder symptoms, but are not limited thereto.

The female menopause symptoms can be alleviated by increasing the decreased female hormone levels in the blood or enhancing the degraded activities of female hormones.

According to an embodiment of the present invention, pinitol or a pinitol-like compound or D-chiro-inositol or a D-chiro-inositol-like compound, which are the active ingredient of the present invention, increases the level of 17β-estradiol, one of the female hormone estrogens, in the blood.

According to another embodiment of the present invention, pinitol or a pinitol-like compound or D-chiro-inositol or a D-chiro-inositol-like compound, which are the active ingredient of the present invention, decreases the sex-hormone binding globulin (SHBG) level in the blood.

The "sex-hormone binding globulin (SHBG)" is a protein that is produced by the liver and present in the blood. The SHBG binds to a sex hormone, for example, testosterone, dihydrotestosterone, or 17β-estradiol, to deliver the hormones in an inactivated state through the blood. Only a very small proportion, for example, about 1-2%, of sex hormones are present in a free state that is not bound to SHBG, and only these free sex hormones enter cells and bind to receptors, showing biological activity. In this sense, SHBG can inhibit the functions of the sex hormones, and the bioavailability of sex hormones is influenced by the SHBG level in the blood. Therefore, when the sex hormone levels in the blood are lower than normal ranges, the lowering of the sex-hormone binding globulin level in the blood has an effect of maintaining the activities of sex hormones in actual tissues in normal ranges.

In the present invention, the pharmaceutical composition is provided in the form of a pharmaceutical composition for treatment or prevention of female menopause symptoms, the pharmaceutical composition containing: (a) a pharmaceutically effective amount of pinitol or a pinitol-like compound or D-chiro-inositol or a D-chiro-inositol-like compound; and (b) a pharmaceutically acceptable carrier.

As used herein, the term "prevention" refers to suppressing the occurrence of disorders or diseases in animals not diagnosed to have but are susceptible to such disorders or diseases.

As used herein, the term "treatment" refers to (i) suppressing the development of disorders or diseases; (ii) reducing disorders or diseases, or (iii) removing disorders or diseases.

The pharmaceutically acceptable carrier contained in the pharmaceutical composition of the present invention is usually used at the time of formulation, and includes carbohydrate-based compounds (e.g., lactose, amylose, dextrose, sucrose, sorbitol, mannitol, starch, cellulose, etc.), gum acacia, calcium phosphate, alginate, gelatin, calcium silicate, microcrystalline cellulose, polyvinylpyrrolidone, cellulose, water, syrup, a salt solution, alcohol, gum arabic, vegetable oils (e.g., corn oil, cotton seed oil, soybean oil, olive oil, coconut oil, etc.), polyethylene glycol, methyl cellulose, methyl hydroxy benzoate, propyl hydroxy benzoate, talc, magnesium stearate, and mineral oil, but are not limited thereto.

The pharmaceutical composition of the present invention may further contain, in addition to the above ingredients, a lubricant, a wetting agent, a sweetening agent, a flavoring agent, an emulsifier, a suspending agent, a preservative, and the like. Suitable pharmaceutically acceptable carriers and preparations are described in detail in Remington's Pharmaceutical Sciences (19th ed., 1995).

A suitable dose of the pharmaceutical composition of the present invention may be variously prescribed depending on various factors, such as the method for formulation, the manner of administration, the patient's age, body weight, gender, morbidity, and diet, the time of administration, the route of administration, the excretion rate, and the response sensitivity. Meanwhile, the oral dose of the pharmaceutical composition of the present invention is preferably 0.001-1000 mg/kg (body weight) per day.

The pharmaceutical composition of the present invention may be formulated in a unit dosage form or into a multi-dose container using a pharmaceutically acceptable carrier and/or excipient according to a method that is easily conducted by a person having ordinary skills in the art to which the present invention pertains. Here, the formulation may be a solution in an oily or aqueous medium, a suspension, an emulsion, an extract, a powder, granules, a tablet, or a capsule, and may further contain a dispersant or a stabilizer.

In accordance with another aspect of the present invention, there is provided a method for prevention or treatment of female menopause symptoms, the method including administering a composition to a subject in need thereof, the composition containing pinitol or a pinitol-like compound or D-chiro-inositol or a D-chiro-inositol-like compound as an active ingredient.

As used herein, the term "administration" or "administer" refers to the direct application of a therapeutically effective amount of the composition of the present invention to a subject (i.e., an object) in need of the composition, thereby forming the same amount thereof in the body of the subject. Therefore, the term "administration" includes the injection of the composition of the present invention around a site of lesion, and thus the term "administer" is used in the same meaning as "inject".

The "therapeutically effective amount" of the composition means a content of the composition, which is sufficient to provide a therapeutic or prophylactic effect to a subject to who the composition is to be administered, and thus the term has a meaning including "prophylactically effective amount". As used herein, the term "subject" includes, without limitation to, a human being, mouse, rat, guinea pig, dog, cat, horse, cow, pig, monkey, chimpanzee, beaver, or rhesus monkey. Specifically, the subject of the present invention is a human being.

Since the method for prevention or treatment of female menopause symptoms of the present invention is directed to a method including administering the pharmaceutical composition for prevention or treatment of female menopause symptoms according to an aspect of the present invention, overlapping descriptions therebetween are omitted to avoid excessive complication of the specification.

In accordance with still another aspect of the present invention, there is provided a food composition containing pinitol or a pinitol-like compound or D-chiro-inositol or a D-chiro-inositol-like compound as an active ingredient for prevention or alleviation of female menopause symptoms.

In the present invention, the food composition is provided in the form of a food composition for alleviation or prevention of female menopause symptoms, the food composition containing: (a) a pharmaceutically effective amount of pinitol or a pinitol-like compound or D-chiro-inositol or a D-chiro-inositol-like compound; and (b) a pharmaceutically acceptable carrier.

As used herein, the term "alleviation" refers to the reduction of symptoms caused by diseases or symptoms caused by disease complication.

When the food composition of the present invention is a functional food composition, the food composition may contain, in addition to the active ingredient, ingredients that are usually added in food manufacturing, for example, a protein, a carbohydrate, a fat, a nutrient, a seasoning, and a sweetening agent. Examples of the foregoing carbohydrate may include typical sugars (monosaccharides, such as glucose and fructose; disaccharides, such as maltose, sucrose, and oligosaccharides; and polysaccharides, such as dextrin and cyclodextrin) and sugar alcohols, such as xylitol, sorbitol, and erythritol. Examples of the sweetening agent may include natural sweetening agents (thaumatin, and *stevia* extract (e.g., rebaudioside A, glycyrrhizin, etc.)) and synthetic sweetening agents (saccharin, aspartame, etc.). For example, when the food composition of the present invention is manufactured into a drink, the food composition may further contain, in addition to the pinitol or pinitol-like compound or the D-chiro-inositol or D-chiro-inositol-like compound, which corresponds to the active ingredient of the present invention, citric acid, high fructose corn syrup, sugar, glucose, acetic acid, malic acid, fruit juice, an Eucommia ulmoides extract, a jujube extract, a licorice extract, and the like. Considering easy accessibility to food, the food composition of the present invention is very useful for preventing or alleviating female menopause symptoms.

Features and advantages of the present invention are summarized as follows.

(i) The present invention relates to a use of pinitol or a pinitol-like compound or D-chiro-inositol or a D-chiro-inositol-like compound for prevention or treatment of female menopause symptoms.

(ii) The pinitol or pinitol-like compound or the D-chiro-inositol or D-chiro-inositol-like compound of the present invention has an effect of increasing activities of female hormones by increasing the 17β-estradiol level in the blood and decreasing the sex-hormone binding globulin (SHBG) level in the blood, and thus can be developed as a drug or functional food for preventing, alleviating, or treating female menopause symptoms.

(iii) The pinitol or pinitol-like compound or the D-chiro-inositol or D-chiro-inositol-like compound of the present invention is derived from natural products, and thus has very few side effects when applied to the human body, unlike female sex hormones or chemically synthesized derivatives of sex hormones.

Advantageous Effects

The active ingredient compound of the present invention has an effect of increasing activity of female hormones by increasing the level of 17β-estradiol in the blood and decreasing the level of sex-hormone binding globulin in the blood. Therefore, the active ingredient compound of the present invention can be developed as a drug or functional food for prevention, alleviation, or treatment of female menopause symptoms The active ingredient of the present invention is derived from natural products, and thus has very few side effects when applied to the human body, unlike female sex hormones or chemically synthesized derivatives of sex hormones.

DETAILED DESCRIPTION

EXAMPLES

Materials and Methods

1. Administration of Pinitol or D-Chiro-Inositol in White Rats and Preparation of Blood Pinitol and D-chiro-inositol were purchased from Biosearch Life (Camino de Purchil, 66. 18004 Granada, Spain). Six-month-old female Sprague-Dawley (SD) white rats (Orient, Korea) were divided into a test group administered with pinitol or D-chiro-inositol and a control group administered with physiological saline while ten animals were used in the test for each of the groups. The rats were bred in a breeding room controlled under a temperature of 22±1° C., humidity of 55±1%, and 12-hour light/dark cycle. The rats were given free access to food and water, and for 7 days after entrance, the rats were acclimated for the breeding environment, and then were used for tests. Physiological saline and pinitol or D-chiro-inositol were orally administered at various doses (10 mg/kg, 20 mg/kg, or 40 mg/kg) at the same amount once a day for 8 weeks. After the last oral administration, the rats were fasted overnight and then anesthetized with ether, and the abdomen was cut open, and then blood was collected from the abdominal vein. The collected blood was transferred to a heparinized tube, followed by centrifugation at 2.500 rpm for 15 minutes for 4° C., thereby separating serum and plasma. The separated blood was stored at −80° C. until the next test.

2. Administration of Pinitol or D-Chiro-Inositol in Middle-Aged Women and Preparation of Blood Forty middle-aged women aged 40 or more were divided into four groups each having ten women, and the four groups were designated as a control group taking a placebo and three test groups taking pinitol. Similarly, forty middle-aged women aged 40 or more were divided into four groups each having ten women, and the four groups were designated as a control group taking a placebo and three test groups taking D-chiro-inositol. Thereafter, the placebo, pinitol, or D-chiro-inositol was administered at various concentrations for 8 weeks in a double-blind fashion. The pinitol, D-chiro-inositol, or placebo was administered at 600 mg, 1,200 mg, and 2,400 mg a day. The blood was taken from the arm vein at the same time, 2:00 pm, before intake and after the last intake, and then transferred to heparinized tubes, followed by centrifugation at 2,500 rpm (4° C.) for 15 minutes, and therefore, the plasma was separated by transfer to new tubes. The separated plasma was used to measure sex hormone levels in the blood.

3. ELISA Assay

The levels of hormones and proteins in the blood were measured according to the manufacturer's manual by using the ELISA kit (Enzo Life Sciences, U.S.A.) for measurement of 17β-estradiol or sex-hormone binding globulin (SHBG) in the blood.

4. Menopause Rating Scale (MRS) Survey

Since subjective symptoms account for a large proportion of menopausal symptoms, several measures are used to assess the degrees of menopausal clinical symptoms. For assessment of menopausal clinical symptoms, Kupperman's index has been used for a long time. However, questions of vaginal dryness, reduction of sexual desire, and the like, are missing in the Kupperman's index, and therefore, the Menopause Rating Scale (MRS) and the Menopause-Specific Quality of Life Questionnaire (MENQOL), which are questionnaires supplementing such questions, are being widely used in current clinical trials. The MRS has been globally recognized to have reliability and feasibility due to its advantages of having a small number of questions, a total of 11 questions, and being simple and convenient, and thus the MRS is being recited in many studies (Table 1). In the present invention, the severity of menopausal symptoms was measured and analyzed by allowing the above middle-aged women clinical subjects to fill out the MRS questionnaire. The alleviating effects on female menopause symptoms were assessed by allowing the middle-aged women clinical subjects to fill out the Menopause Rating Scale (MRS) questionnaire pre- and post-intake of the placebo, pinitol, or D-chiro-inositol.

TABLE 1

| Symptoms | Condition extent (Score) | | | | |
| --- | --- | --- | --- | --- | --- |
| | None (0) | Mild (1) | Moderate (2) | Severe (3) | Extremely severe (4) |
| 1. Hot flushes, sweating (abrupt sweating, face burning and being getting a fever) | | | | | |
| 2. Heart discomfort (unusual awareness of heart beat, heart skipping, heart racing, heart tightness) | | | | | |
| 3. Sleep problem (difficulty in falling asleep, waking up frequently, difficulty in sleeping through the night) | | | | | |
| 4. Depressive mood (feeling down, sad, on the verge of tears, lack of drive, mood swings) | | | | | |
| 5. Irritability (feeing nervous, feeling aggressive, inner tension) | | | | | |
| 6. Anxiety (inner restlessness, feeling panicky) | | | | | |
| 7. Physical and mental exhaustion (general decrease in daily life performance, fatigue, helplessness, impaired memory, decrease in concentration, forgetfulness) | | | | | |
| 8. Sexual problems (change in sexual desire, change in sexual activity, change in sexual satisfaction) | | | | | |
| 9. Bladder problems (difficulty in urinating, increased need to urinate, bladder incontinence) | | | | | |
| 10. Dryness of vagina (sensation of dryness or burning in the vagina, difficulty with sexual intercourse) | | | | | |
| 11. Joint and muscular discomfort (pain in the joints, rheumatoid complaints) | | | | | |
| Total | | | | | |

Results

Figure 1:
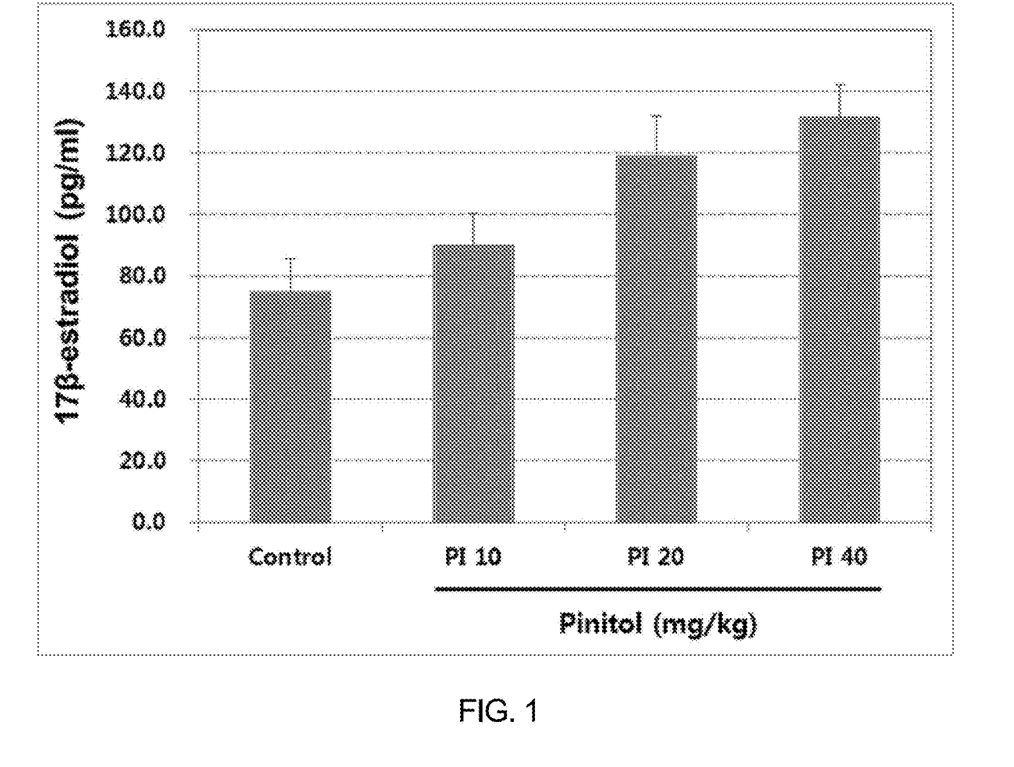
FIG. 1 shows the results of measurement of 17β-estradiol levels in the blood in a control group in which mature female Sprague-Dawley white rats were administered with physiological saline and test groups in which mature female Sprague-Dawley white rats were administered with pinitol of various concentrations (10 mg/kg, 20 mg/kg, and 40 mg/kg).
Figure 2:
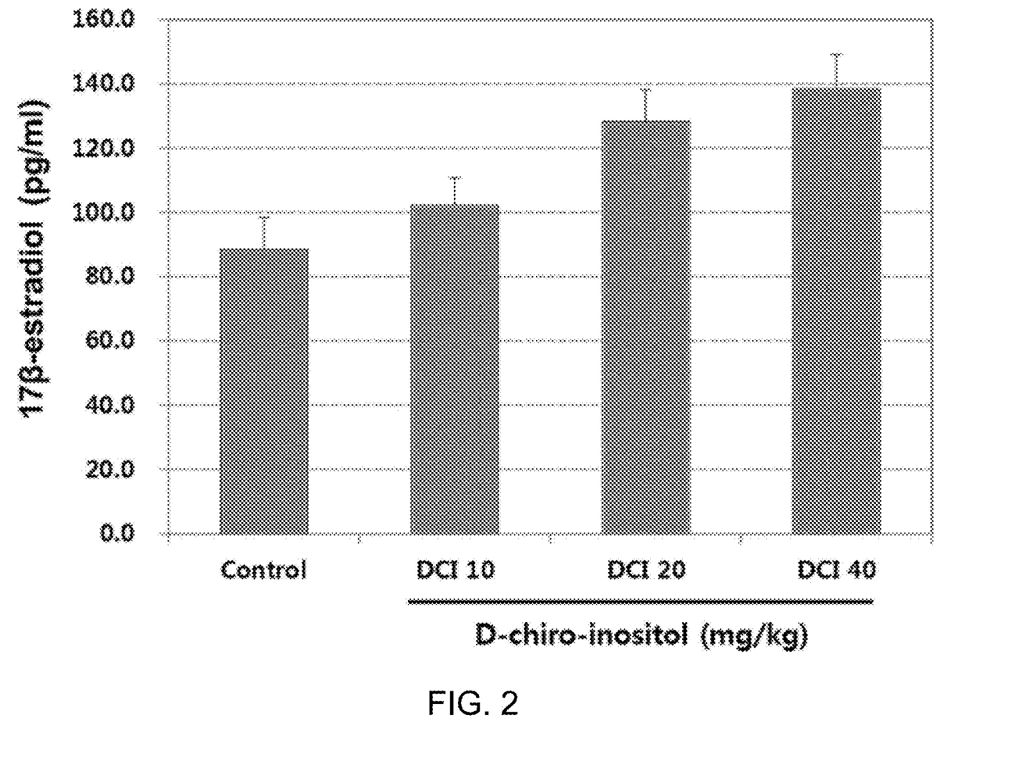
FIG. 2 shows the results of measurement of 17β-estradiol levels in the blood in a control group in which mature female Sprague-Dawley white rats were administered with physiological saline and test groups in which mature female Sprague-Dawley white rats were administered with D-chiro-inositol of various concentrations (10 mg/kg, 20 mg/kg, and 40 mg/kg).
Figure 3:
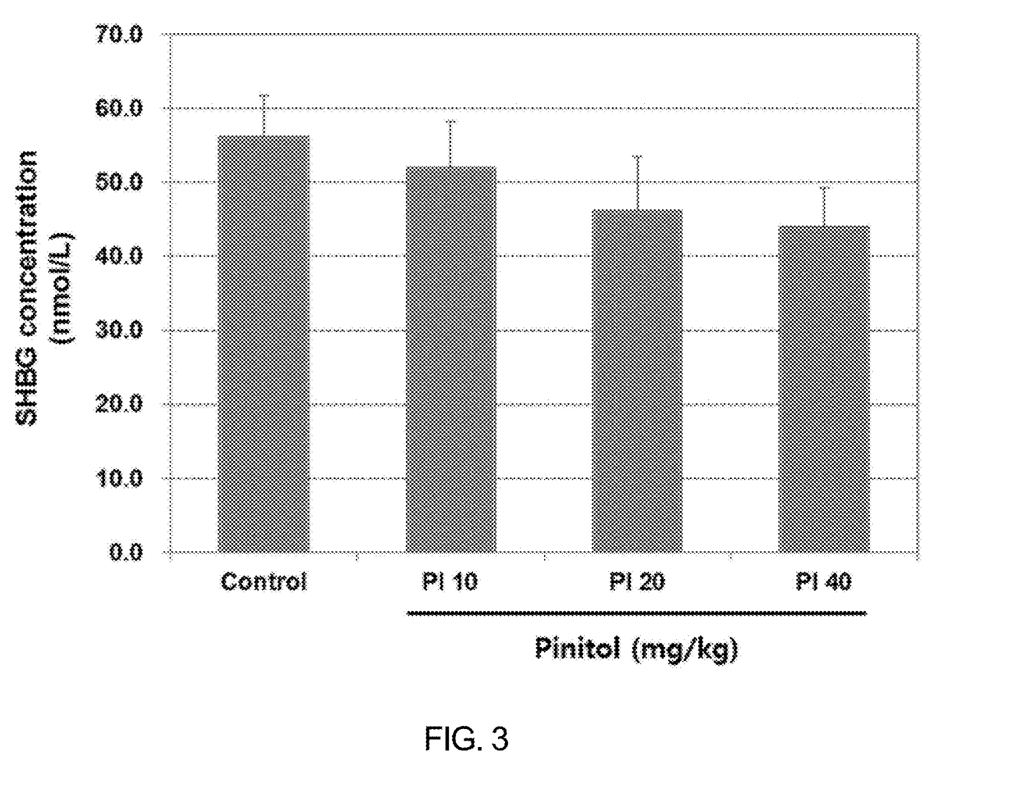
FIG. 3 shows the results of measurement of sex-hormone binding globulin (SHBG) levels in the blood in a control group in which mature female Sprague-Dawley white rats were administered with physiological saline and test groups in which mature female Sprague-Dawley white rats were administered with pinitol of various concentrations (10 mg/kg, 20 mg/kg, and 40 mg/kg).
Figure 4:
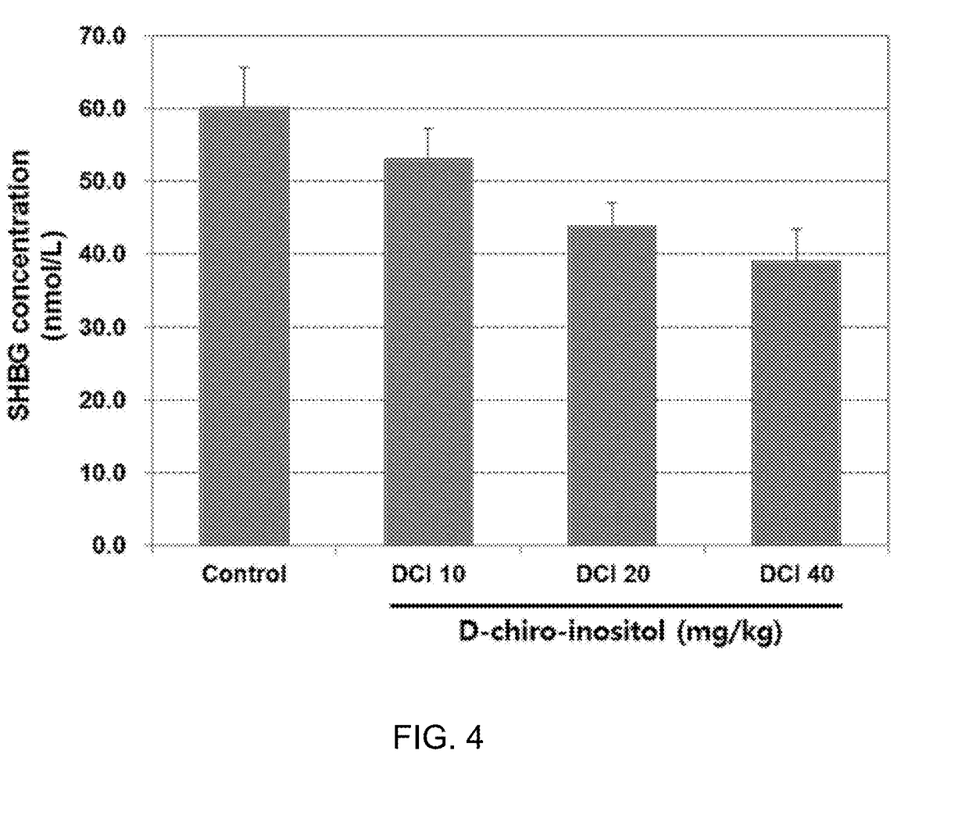
FIG. 4 shows the results of measurement of SHBG levels in the blood in a control group in which mature female Sprague-Dawley white rats were administered with physiological saline and test groups in which mature female Sprague-Dawley white rats were administered with D-chiro-inositol of various concentrations (10 mg/kg, 20 mg/kg, and 40 mg/kg).

1. Analysis of Effect of Pinitol or D-Chiro-Inositol on Levels and Activity of Female Hormones in White Rats In order to analyze the effects of pinitol or D-chiro-inositol (DCI) on the levels or activity of female hormones, which are blood indexes associated with menopausal symptoms, in female mature Sprague-Dawley (SD) white rats, a test was conducted. The physiological saline for the control group or pinitol or D-chiro-inositol (10 mg/kg, 20 mg/kg, and 40 mg/kg) for the test groups were orally administered at the predetermined time once a day for 8 weeks. After the completion of the last administration, the 17β-estradiol and sex-hormone binding globulin (SHBG) levels in the blood were measured by ELISA kit. As a result of the test, compared with the 17β-estradiol level in the blood in the mature white rats administered with physiological saline in the control group, the 17β-estradiol levels in the blood in the mature white rats in the test groups significantly increased in a concentration-dependent manner of pinitol or D-chiro-inositol (FIGS. 1 and 2). The level of SHBG, which binds with sex hormones to inhibit activity thereof in the body, in the blood decreased in the pinitol 10 mg/kg, 20 mg/kg, and 40 mg/kg administration groups by about 4.2 nmol/L, 10.0 nmol/L, and 12.2 nmol/L, respectively, and in the D-chiro-inositol 10 mg/kg, 20 mg/kg, and 40 mg/kg administration groups by about 7.0 nmol/L, 16.2 nmol/L, and 21.1 nmol/L, respectively, when compared with the control group (FIGS. 3 and 4). Therefore, it could be confirmed that the SHBG level in the blood was decreased by pinitol or D-chiro-inositol, leading to increases in activity of female hormones. According to the test results, it was confirmed that both pinitol and D-chiro-inositol can alleviate female menopause symptoms by increasing the 17β-estradiol levels in the blood and decreasing the SHBG levels in the blood.

Figure 5:
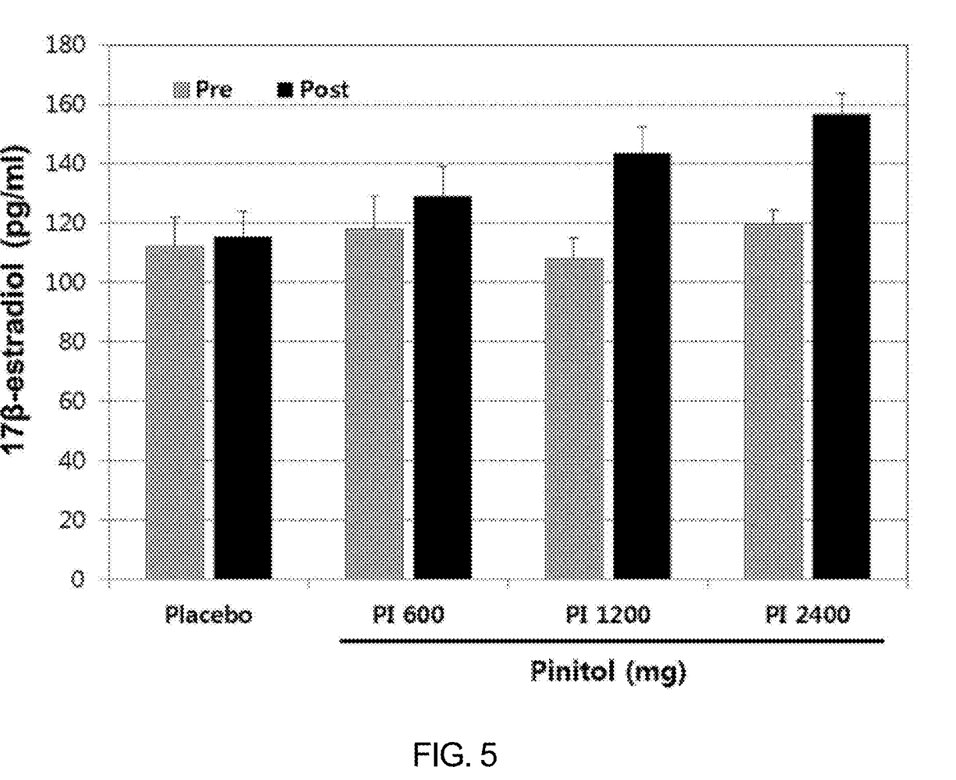
FIG. 5 shows the results of measurement of pre- and post-administration 17β-estradiol levels in the blood in a control group in which menopausal women were administered with placebo and test groups in which menopausal women were administered with pinitol of various concentrations (600 mg, 1,200 mg, and 2,400 mg).
Figure 6:
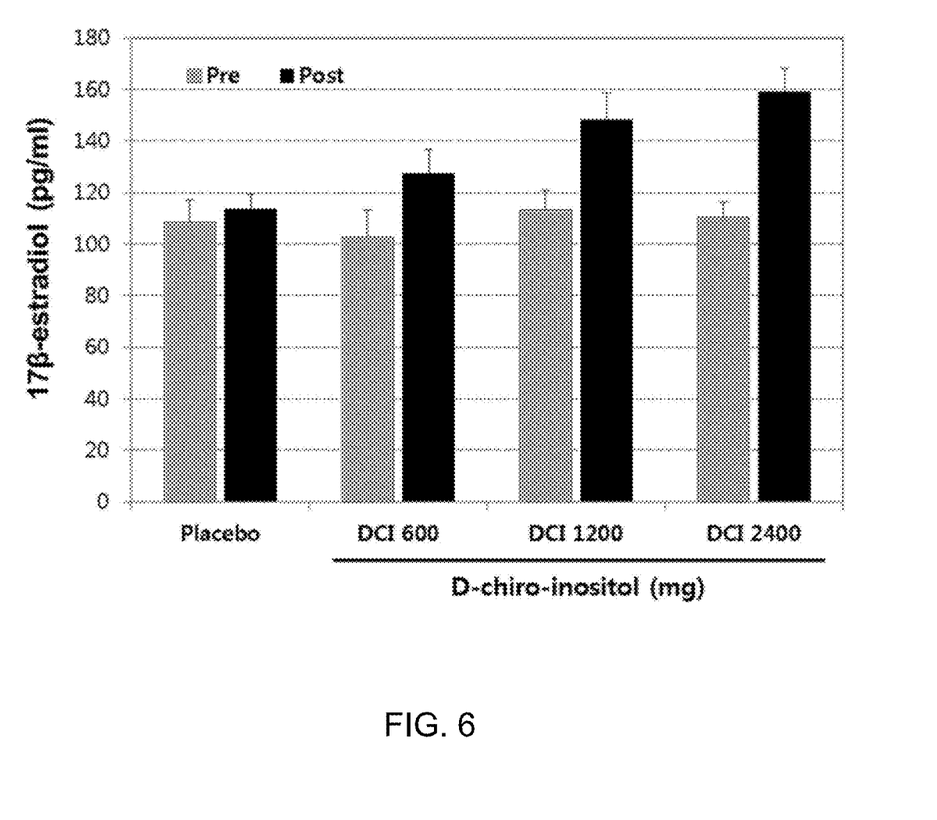
FIG. 6 shows the results of measurement of pre- and post-administration 17β-estradiol levels in the blood in a control group in which menopausal women were administered with placebo and test groups in which menopausal women were administered with D-chiro-inositol of various concentrations (600 mg, 1,200 mg, and 2,400 mg).
Figure 7:
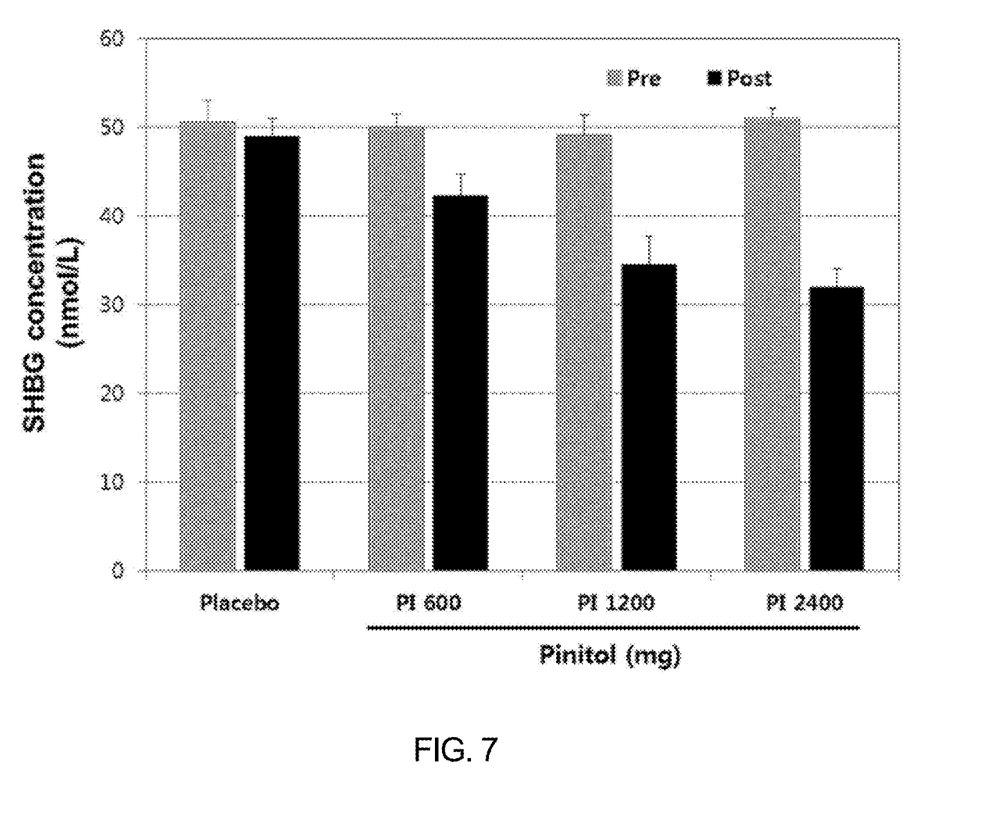
FIG. 7 shows the results of measurement of pre- and post-administration SHBG levels in the blood in a control group in which menopausal women were administered with placebo and test groups in which menopausal women were administered with pinitol of various concentrations (600 mg, 1,200 mg, and 2,400 mg).
Figure 8:
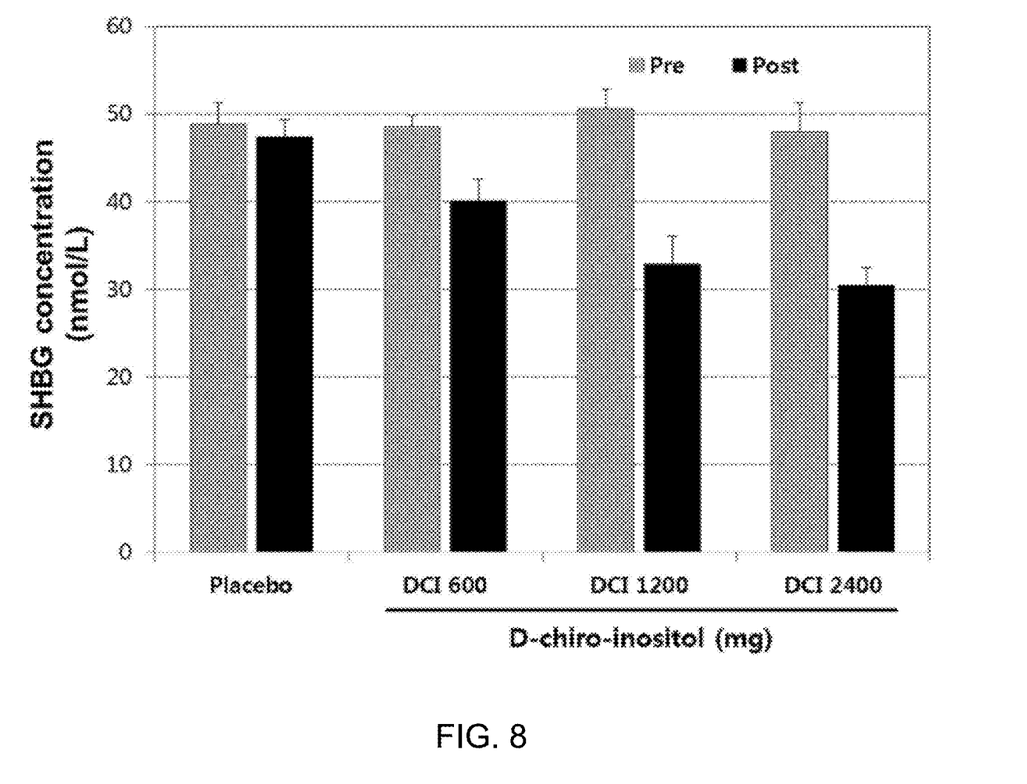
FIG. 8 shows the results of measurement of pre- and post-administration SHBG levels in the blood in a control group in which menopausal women were administered with placebo and test groups in which menopausal women were administered with D-chiro-inositol of various concentrations (600 mg, 1,200 mg, and 2,400 mg).

2. Analysis of Effect of Pinitol or D-Chiro-Inositol on Levels and Activity of Female Hormones in Middle-Aged Women In order to analyze the effects of pinitol and D-chiro-inositol on sex hormones in middle-aged women, forty middle-aged 40 or more were divided into four groups each having ten women, and the four groups were designated as a control group taking a placebo and three test groups taking pinitol. Similarly, forty middle-aged women aged 40 or more were divided into four groups each having ten women, and the four groups were designated as a control group taking a placebo and three test groups taking D-chiro-inositol. Thereafter, the placebo, pinitol, or D-chiro-inositol was administered at various concentrations for 8 weeks in a double-blind fashion. The pinitol or D-chiro-inositol was administered at 600 mg, 1,200 mg, and 2,400 mg a day for 8 weeks. As a result of the test, there was no significant change in 17β-estradiol level in the blood in the women between pre- and pro-administration of the placebo. Also, there was no particular difference between pre- and post-administration of pinitol or D-chiro-inositol. However, the 17β-estradiol level in the blood significantly increased in a concentration-dependent manner of pinitol or D-chiro-inositol in the pinitol or D-chiro-inositol administration groups compared with the placebo administration group (FIGS. 5 and 6). Similarly, there was no particular difference in SHBG level in the blood between pre- and post-administration of the placebo and between pre- and post-administration of the pinitol. However, the SHBG levels in the blood decreased in the pinitol 600 mg, 1,200 mg, and 1,400 mg administration groups by about 8.3 nmol/L, 16.0 nmol/L, and 18.6 nmol/L, respectively, and in the D-chiro-inositol 600 mg, 1,200 mg, and 1,400 mg administration groups by about 8.7 nmol/L, 15.9 nmol/L, and 18.4 nmol/L, respectively, when compared with the placebo administration group (FIGS. 7 and 8). According to the test results, it could be confirmed that, similar to the results in the white rats, pinitol and D-chiro-inositol can alleviate female menopause symptoms by increasing the 17β-estradiol levels in the blood and decreasing the SHBG levels in the blood.

Figure 9:
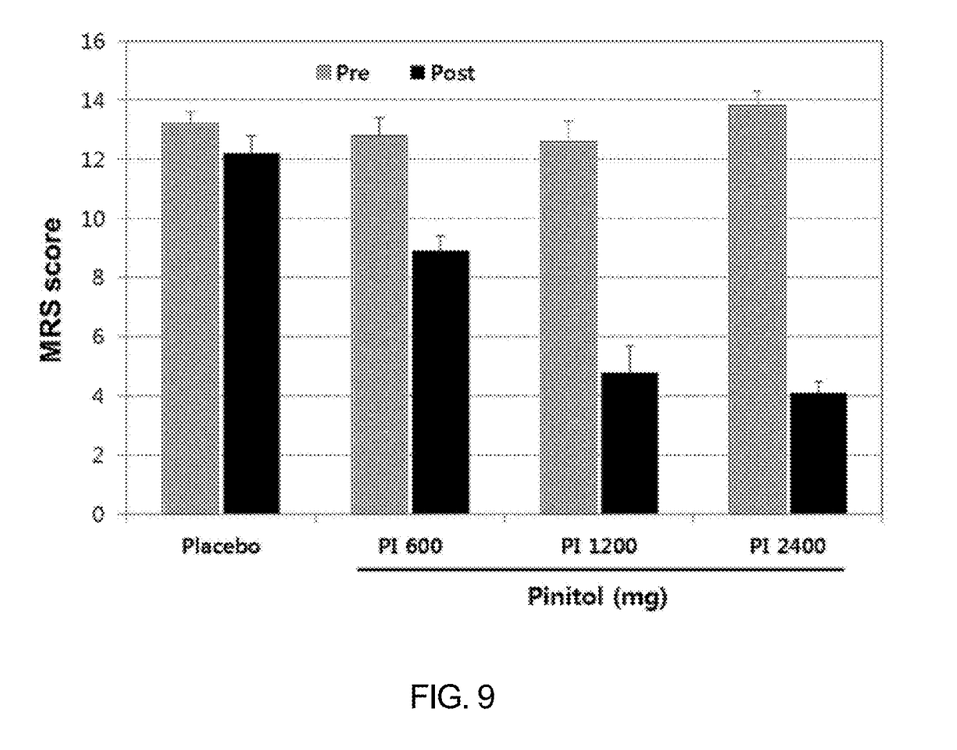
FIG. 9 shows the results of calculation and analysis of pre- and post-administration Menopause Rating Scale (MRS) scores in a control group in which menopausal women were administered with placebo and test groups in which menopausal women were administered with pinitol of various concentrations (600 mg, 1,200 mg, and 2,400 mg).
Figure 10:
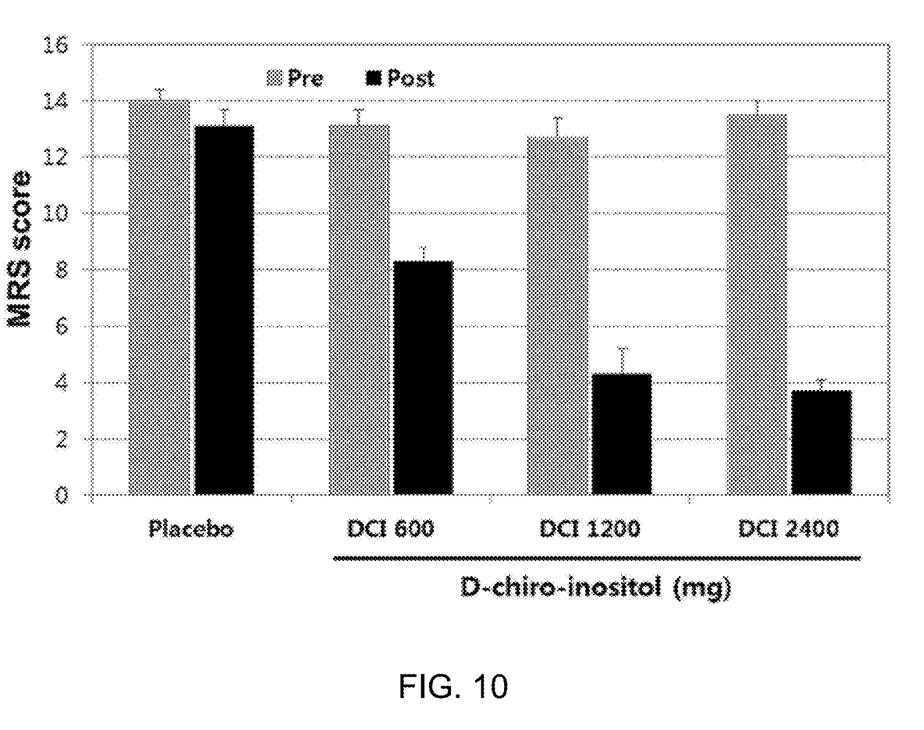
FIG. 10 shows the results of calculation and analysis of pre- and post-administration Menopause Rating Scale (MRS) scores in a control group in which menopausal women were administered with placebo and test groups in which menopausal women were administered with D-chiro-inositol of various concentrations (600 mg, 1,200 mg, and 2,400 mg).

3. Assessment of Prophylactical Effect of Menopausal Symptoms Through Menopause Rating Scale Survey in Middle-Aged Women In order to assess the alleviating effects of female menopause symptoms by pinitol and D-chiro-inositol, a Korean-version Menopause Rating Scale (MRS) survey was performed. Eighty middle-aged 40 or more were divided into four groups, a placebo group and pinitol administration groups, each having ten women, and similarly, were divided into four groups, a placebo group and D-chiro-inositol administration groups, each having ten women. Thereafter, the placebo and 600 mg, 1,200 mg, and 2,400 mg of pinitol or D-chiro-inositol were administered once a day for 8 weeks in a double-blind fashion. The women were allowed to fill out the Menopause Rating Scale (MRS) questionnaire before and after taking the placebo, pinitol, or D-chiro-inositol. The scores of the MRS questionnaire were calculated as a total score. The 0-4 points indicate a good menopausal state, which is a smooth menopause state. A total of 5-8 points indicate a slight menopausal state, requiring management. A total of 9-15 points indicate a severe menopausal state, requiring precise diagnosis and treatment by specialists because of menopausal diseases. Last, a total of 16 points or more indicates an extremely severe menopausal state, thereby urgently requiring therapy through minute management and long-term plans. There was no MRS score difference among pre-taking of placebo, post-taking of placebo, and pre-taking of pinitol or pre-taking of D-chiro-inositol, but the MRS score significantly decreased post-taking of pinitol or D-chiro-inositol compared with the placebo taking group and pre-taking of pinitol and D-chiro-inositol. The average MRS score decreased in the pinitol 600 mg, 1,200 mg, and 2,400 mg administration groups, compared with the placebo group, by 4.3 points, 8.4 points, and 9.1 points, respectively, indicating alleviation rates of menopausal symptoms of about 32.6%, 63.6%, and 68.9%, respectively. In addition, the average MRS score decreased in the D-chiro-inositol 600 mg, 1,200 mg, and 2,400 mg administration groups, compared with the placebo group, by 5.7 points, 9.7 points, and 10.3 points, respectively, indicating alleviation rates of menopausal symptoms of about 40.7%, 69.3%, and 73.6%, respectively. The results showed the alleviating effects of female menopausal diseases by pinitol and D-chiro-inositol in a concentration-dependent fashion (FIGS. 9 and 10). The MRS measurement results could confirm that pinitol alleviated female menopause symptoms caused by female hormone reduction, such as reduction of sexual desire, insomnia, urogenital diseases and infections, joint and muscular diseases, depression, and hypersensitiveness.

The specific embodiments described herein are representative of preferred embodiments or examples of the present invention, and thus the scope of the present invention is not limited thereto. It would be apparent to those skilled in the art that modifications and other uses of the invention do not depart from the scope of the invention described in the claims.

What is claimed is:

1. A method for treatment or alleviation of female menopausal symptoms, the method comprising administering, to a subject, a composition comprising pinitol as an active ingredient, and
   wherein the pinitol is administered at a dose of between 600 mg and 2,400 mg per day.

2. The method of claim 1, wherein the composition increases the level of 17β-estradiol in the blood.

3. The method of claim 1, wherein the composition decreases the level of sex-hormone binding globulin (SHBG) in the blood.

* * * * *